(12) United States Patent
Jespersen et al.

(10) Patent No.: US 7,597,679 B2
(45) Date of Patent: Oct. 6, 2009

(54) SAFETY SYSTEM FOR AN ELECTRICALLY DRIVEN MEDICAL DELIVERY DEVICE AND A COMPUTER-READABLE MEDIUM

(75) Inventors: Soren Kragh Jespersen, Sorup (DK); Jens Aage Munk, Olstykke (DK); Jim Radmer, Fredensborg (DK); Jens Ulrik Poulsen, Virum (DK); Lars Hofmann Christensen, Jyllinge (DK); Lars Peter Klitmose, Gentofte (DK)

(73) Assignee: Novo Nordisk A/S, Bagsvaerd (DK)

( * ) Notice: Subject to any disclaimer, the term of this patent is extended or adjusted under 35 U.S.C. 154(b) by 568 days.

(21) Appl. No.: 10/397,913

(22) Filed: Mar. 26, 2003

(65) Prior Publication Data

US 2003/0231116 A1  Dec. 18, 2003

Related U.S. Application Data

(60) Provisional application No. 60/376,460, filed on Apr. 30, 2002.

(30) Foreign Application Priority Data

Mar. 27, 2002   (DK) ............................... 2002 00468

(51) Int. Cl.
*A61M 31/00* (2006.01)
(52) U.S. Cl. .......................................... 604/65; 417/17
(58) Field of Classification Search ................... 604/65, 604/154, 155, 66, 67; 340/635; 700/282; 600/432; 128/DIG. 1; 417/17, 18
See application file for complete search history.

(56) References Cited

U.S. PATENT DOCUMENTS

| | | | |
|---|---|---|---|
| 4,498,843 A | * | 2/1985 | Schneider et al. ............. 417/22 |
| 4,722,734 A | | 2/1988 | Kolln ......................... 604/151 |
| 4,897,184 A | | 1/1990 | Shouldice et al. ............. 210/87 |
| 4,908,017 A | * | 3/1990 | Howson et al. ............... 604/67 |

(Continued)

FOREIGN PATENT DOCUMENTS

DE    0800979    *   9/1996

(Continued)

OTHER PUBLICATIONS

Office Action issued in connection with counterpart Danish Application No. PA 2002/00468, mailed Nov. 15, 2002.

(Continued)

*Primary Examiner*—Nicholas D Lucchesi
*Assistant Examiner*—Christopher D Koharski
(74) *Attorney, Agent, or Firm*—Wesley A. Nicolas

(57) ABSTRACT

This invention relates to a safety system for an electrically driven medical delivery device for delivering a dose of medication, wherein the safety system is configured for preventing delivery of an erroneous dose of the medicament and comprising detector means for registering mechanical movement, the system comprising at least two detector means (10, 11) for detecting a mechanical parameter and for emitting signals to control circuits (14, 15) configured for controlling the rower supply to driving means (12) for the delivery device. Further, this invention relates to a computer-readable medium comprising a program for controlling a delivery device etc. This allows providing a system that works very quickly, accurately and reliable as to preventing an erroneous dose of medication.

14 Claims, 1 Drawing Sheet

U.S. PATENT DOCUMENTS

| | | | | |
|---|---|---|---|---|
| 5,532,562 | A | | 7/1996 | Yasuda .................. 318/439 |
| 5,613,935 | A | * | 3/1997 | Jarvik ..................... 600/16 |
| 5,681,285 | A | * | 10/1997 | Ford et al. ............. 604/151 |
| 5,791,880 | A | * | 8/1998 | Wilson .................... 417/14 |
| 5,889,376 | A | | 3/1999 | Takatsuka et al. |
| 6,259,587 | B1 | | 7/2001 | Sheldon et al. .......... 361/23 |
| 6,410,993 | B1 | | 6/2002 | Giers |
| 6,808,508 | B1 | * | 10/2004 | Zafirelis et al. ........ 604/131 |
| 7,128,729 | B2 | * | 10/2006 | Duchon et al. ......... 604/154 |

FOREIGN PATENT DOCUMENTS

| | | | |
|---|---|---|---|
| EP | 0 028 364 | A2 | 5/1981 |
| EP | 0 118 008 | A2 | 9/1984 |
| EP | 0 384 155 | | 8/1990 |
| EP | 0 800 979 | A2 | 10/1997 |
| EP | 0800979 | * | 10/1997 |
| EP | 1 102 378 | A2 | 11/2000 |
| GB | 2 150 373 | A | 6/1985 |
| JP | H9-285182 | | 10/1997 |

OTHER PUBLICATIONS

International Search Report issued in connection with counterpart PCT Application No. PCT/DK03/00205, mailed Jul. 7, 2003.

Written Opinion issued in connection with counterpart PCT Application No. PCT/DK03/00205, mailed Jan. 14, 2004.

International Preliminary Examination Report issued in connection with counterpart PCT Application No. PCT/ DK03/00205, mailed May 18, 2004.

Office Action issued in connection with counterpart Russian Application No. 2004131650/(034118), mailed Nov. 17, 2004.

Office Action issued in connection with counterpart Chinese Application No. 03807103.7, mailed Sep. 1, 2006.

Office Action issued in connection with counterpart Chinese Application No. 03807103.7, mailed Apr. 27, 2007.

English language translation of Office Action issued in counterpart Japanese Patent Application No. 2003-577983 mailed Mar. 10, 2009.

* cited by examiner

SAFETY SYSTEM FOR AN ELECTRICALLY DRIVEN MEDICAL DELIVERY DEVICE AND A COMPUTER-READABLE MEDIUM

CROSS-REFERENCE TO RELATED APPLICATIONS

This application claims priority under 35 U.S.C. 119 of Danish application No. PA 2002 00468 filed Mar. 27, 2002 and U.S. provisional application No. 60/376,460 filed Apr. 30, 2002; the contents of both are fully incorporated herein by reference.

The invention relates to a safety system for an electrically driven medical delivery device for delivering a dose of a medication, wherein the safety system is configured for preventing delivery of an erroneous dose of the medicament and comprising detector means for registering mechanical movement.

Systems of that kind are known e.g. from U.S. Pat. No. 6,259,587, which teaches the use of microprocessors having feedback from a detector means for increasing the safety against erroneous dose.

U.S. Pat. No. 4,722,734 comprises the use of a tachometer, and it also mentions the option of increasing the safety by building a time limitation into the safety system.

EP 384 155 comprises a pair of redundant control circuits comprising sensors for detecting whether the delivery device is active.

Developments within pumps and the like equipment for dispensing a dose of medication have become increasingly sophisticated such that, today, doses can be dispensed relatively expediently and, besides, increasingly concentrated medicaments are used, which means that the systems known so far have not provided a sufficient degree of safety against overdoses, due to the prior art systems having more or less presupposed that the dose was administered over such protracted period of time that an upper time limit was sufficient to effectively ensure that an overdose was not delivered.

This is demonstrated with reference to FIG. 3 in the drawing. The full line shows the delivery of a normal dose within a normal time and the dashed line shows 25% overdose within the normal time, if—it happens—two out of ten disk holes in a commonly used detector means are blocked. An overdose of 25% of the most modern insulin types may be lethal.

It is the object of the invention to provide a system that works very quickly, accurately and reliably, i.e. reacts very swiftly in case conditions are detected that seem to point to an overdose. This object may be provided without a limit of time and further even though one of the safety control circuits may fail.

This object is achieved by the safety system comprising at least two control circuits configured for controlling the power supply to driving means for the delivery device; and wherein at least two detector means are provided each being arranged for detecting a mechanical parameter for delivering the dose and for emitting a signal to a respective one of said control circuits.

The high demands made today to the accuracy of delivery of dose and to a safety system being able to expediently preventing an overdose are fulfilled in that both safety circuits receive information from separate, respective detector means, said information being based on a reliable measurement of the mechanical movements that operate the medical delivery device. Such advantageous properties are obtained no matter how the safety circuits are configured, thus they may be a master and slave circuit or the control circuit may comprise two separately operating control circuits.

A further advantage obtained by two separate detector means is that the signals emitted from the detector means may be processed in the control circuits. Thereby it is possible to take into account any deviation from normal function, e.g. in case of a mismatch a dedicated action can be made in the control circuits.

Preferably the two detector means will be arranged in different places along the mechanical transmission path that originates in the driving means.

A preferred mechanical parameter is a rotational movement that can advantageously be registered by means of an detector means. The detector means can also be configured for detecting a translatory movement, and finally errors in the mechanical movement can further be countered by means of a different control means for blocking the mechanical movement.

Preferably there is a communication connection between the control circuits and a protocol will be determined that defines how the communication may occur.

Preferably the driving means is a DC-driven device, e.g. a motor. For controlling the DC-driven device an H-bridge-coupling of electronic switches can advantageously be provided that is controlled by the control circuits thereby enabling the motor to be controlled in both directions and such that each of the control circuits is capable of forcing the motor to halt, irrespective of its direction of running. This is achieved by the current through the DC-driven device passing a pair of switches that are each controlled by each control circuit.

According to a preferred embodiment the control circuits themselves control the electronic switches before a dose is dispensed, and as a further safety measure the invention can by supplemented by a time monitoring device.

According to a preferred embodiment the safety system according to the invention comprises a microprocessor, and the invention also relates to a computer-readable medium containing a program for making a processor carry out safety operations on a system comprising an electrically driven medical delivery device for delivering a dose of medication, wherein the system is configured for preventing delivery of an erroneous dose of the medicament.

The computer-readable medium is characterised in that the safety operations comprises:
providing two safety routines, each of which depends on an input signal from the detector means for registering mechanical movement; and wherein each safety routine provides an output signal for controlling driving means for the medical delivery device.

BRIEF DESCRIPTION OF THE DRAWINGS

The accompanying drawings illustrate the present invention by way of the embodiments in which.

DETAILED DESCRIPTION OF EMBODIMENTS

Figure 1:
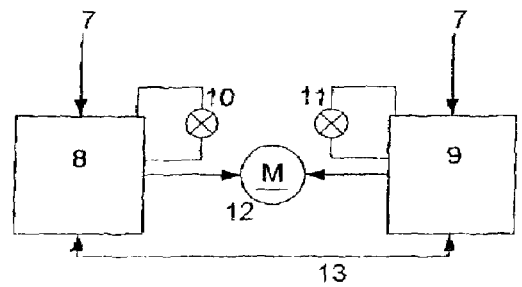
FIG. 1 illustrates a preferred embodiment of the invention with two detector means and the where the control circuits are in an independent configuration.

FIG. 1 shows an embodiment of the invention including two independent control circuits (8, 9), where the control circuits (8, 9) may both be started from an external signal (7), which further does not necessarily emerge from the same source. However, in preferred embodiments the control circuits may have a common communication (13) link among each other for exchanging information such as status, synchronization i.e.

According to the invention each control circuit (8, 9) comprise detector means (10, 11) being fully independent. That is, they do not depend on each other, nor do they necessarily acquire signals from the same injection related mechanical movement. Detector means (10) of the first control circuit (8) could for example sample directly on the driving means (12), where the detector means (11) of the second control circuit (9) may sample on another injection related mechanical movement along the transmission path that originates in the driving means such as the movement of a piston rod (not showed). Another typical and useful placement of the detector means (10, 11) would be in a gearbox to monitor the rotation of the gearwheels. If for some reasons, a gearwheel does not turn, i.e. due to mechanical breakdown, (moisture) etc. the detector means may alert the matching control circuit to perform any appropriate action.

Figures 3, 4:
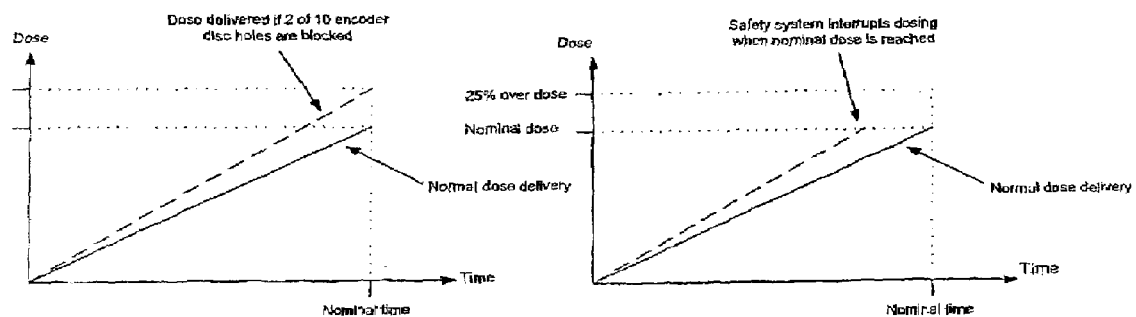
FIG. 3 illustrates a prior art problem.
FIG. 4 illustrates an effect of the invention.

With a reference to FIG. 4 it can be understood that an overdose as explained in connection with FIG. 3 can be obviated. If for example the main detector means has ten holes of which two are blocked then the further separate detector means according to the invention will interrupt the delivery when the nominal dose has been delivered. It should be noted that the invention is not solely understood by referring to FIG. 4, but a substantial part of the invention consists in realizing the problem explained in connection with FIG. 3.

Figure 2:
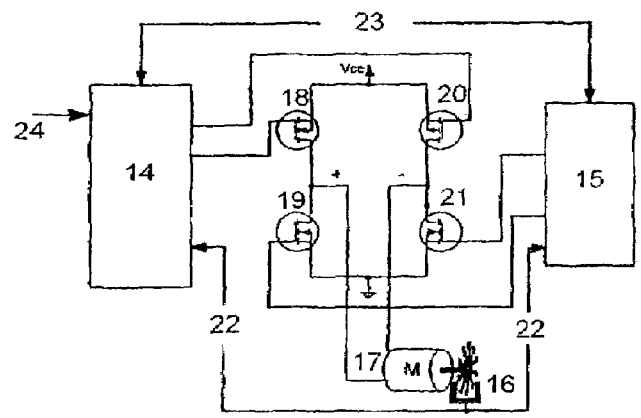
FIG. 2 illustrates another embodiment of the invention with a H-bridge and a DC-motor.

FIG. 2 illustrates a safety system with two control circuits (14, 15) but where only one detector means (16) monitoring a mechanical movement is shown for the sake of clarity. Driving means (17) are connected to a H-bridge formed by switching means (18, 19, 20, 21) where the switches may be formed by i.e. gates, transistors etc. Detector means (16) are mounted on the driving means (17), which may be a motor, gearbox, piston rod etc., providing a signal (22) by the rotation or translatory movements of the driving means. The detector means signal is fed to the two independent control circuits (14, 15), which in this example are in a master/slave configuration wherein the master circuit (14) receives an external signal (24). The master (14) may remove the supply to the driving means (17) by turning off the switches (18, 20), and the slave (15) may turn off the supply to the driving means (17) by turning off the switches (19, 21). Further, a bidirectional communication possibility exists between the master and the slave circuits (23).

The operation before, during and after injection could be as follows:

1. Each switch in the bridge is tested individually.
2. The detector means are tested.
3. The master communicates the selected dose to the slave.
4. The slave calculates the expected injection time and number of detector means pulses.
5. The slave turns on the appropriate switch in the H-bridge.
6. The master signals to the slave that injection is to begin.
7. The master controls the appropriate switch in the H-bridge to obtain the desired injection speed.
8. During injection the slave monitors time and detector means counts and turns off the relevant switch to disable the driving means if expected time or detector means pulses are exceeded.
9. The master disables the relevant switch when it detects that the desired detector means pulses are reached or if any error, e.g. time-out is encountered.
10. The master inquires the slave about status, which may be information whether the injection ended normally, detector means counts exceeded etc.
11. Each switch in the H-bridge is tested individually.

According to the invention two or more individual detector means are used to give feedback about mechanical movements to the master and slave. They may be mounted on a single part of the mechanical system or as preferred, on separate parts of the mechanical system.

The control circuits may be micro controllers or any similar programmable or any suitable device. Detector means may comprise a tachometer, optical sensor or other detector means and any combination thereof. The driving means may comprise an electrically DC-driven motor, a pump etc. In addition to the said safety system with the ability to turn off the relevant switches, a system is preferred where one or more of the control circuits have control of an additional safety appliance, which exists for blocking the mechanical movement of the driving means. This could be made e.g. in the form of a solenoid mounted with a tap that blocks said movement.

Further, the invention also comprises a computer readable medium containing a program for making a processor carry out safety operations The program provides two safety routines, each of which depends on an input signal from separate detector means for registering mechanical movement, and each safety routine provides an output signal for controlling driving means for the medical delivery device.

A computer readable medium may in this context be a program storage medium i.e. both physical computer ROM and RAM, removable alike non-removable storage drives, magnetic tape, optical disc, digital video disk (DVD), compact disc (CD or CD-ROM), mini-disc, hard disk, floppy disk, smart card, PCMCIA card, information acquired from data networks e.g. a local area network (LAN), a wide area network (WAN), or any combination thereof, e.g. the Internet, an intranet, an extranet, etc.

That is, a dedicated device with e.g. embedded safety control routines, memory storage and controlling arrangements as well as any remote controllable systems according to the present invention is covered in the claims.

The invention claimed is:

1. A safety system for an electrically driven medical delivery device for delivering a dose of a medicament, wherein the safety system is configured for preventing delivery of an erroneous dose of the medicament and comprising:
   at least one detector, said safety system comprising: at least two control circuits wherein a communication connection is provided between the control circuits, each configured for independently controlling a power supply to a driving means of the delivery device which is configured to deliver a dose of medicament, and
   the at least one detector connected to each control circuit, each detector being arranged in a different place along a mechanical transmission path of the delivery device, and each detector being arranged for separately detecting a mechanical parameter of delivering the dose of medicament and for emitting a signal to its respective control circuit, wherein each detector and its respective control circuit is arranged to operate the driving means of the delivery device independently from each other detector and its respective control circuit,
   wherein during injection the at least two control circuits monitor time and a mechanical parameter of the at least one detector, whereby at least one of the at least two control circuits disable the driving means if the time or mechanical parameter exceeds an expected value indicative of a nominal dose of a medicament, thereby preventing delivery of an erroneous dose of medicament.

2. A safety system according to claim 1, wherein the control circuits comprise a master circuit and a slave circuit.

3. A safety system according to claim 1, wherein the control circuits comprise two separately operating control circuits.

4. A safety system according to claim 1, wherein the output signals from the detector are processed in the control circuits for fault detection.

5. A safety system according to claim 1, wherein the driving means is a DC-driven device.

6. A safety system according to claim 1 wherein the detector means are configured for detecting a rotational movement.

7. A safety system according to claim 1, wherein the detector means are configured for detecting a translational movement.

8. A safety system according to claim 1, further comprising additional control means for blocking the mechanical movement.

9. A safety system according to claim 1 wherein the driving means comprise a DC-driven device.

10. A safety system according to claim 9, further comprising electronic switches connected to the control circuits such that the current through the DC-driven device passes a pair of switches that are each controlled by each their control circuits.

11. A safety system according to claim 5, wherein the DC-driven device is connected to the centers of a H-bridge coupling of electronic switches that are connected to a power supply source and that are controlled by the control circuits.

12. A safety system according to claim 11, wherein the control circuits are configured for testing said electronic switches prior to delivery of the dose.

13. A safety system according to claim 1, wherein at least the one control circuit comprises a time monitoring device.

14. A safety system according to claim 1, wherein the communication link connecting the at least two control circuits is configured to exchange information.

* * * * *

UNITED STATES PATENT AND TRADEMARK OFFICE
CERTIFICATE OF CORRECTION

PATENT NO. : 7,597,679 B2  Page 1 of 1
APPLICATION NO. : 10/397913
DATED : October 6, 2009
INVENTOR(S) : Jespersen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1047 days.

Signed and Sealed this

Twenty-eighth Day of September, 2010

David J. Kappos
*Director of the United States Patent and Trademark Office*